US009872120B2

(12) United States Patent
Hong et al.

(10) Patent No.: US 9,872,120 B2
(45) Date of Patent: Jan. 16, 2018

(54) ULTRASONIC TRANSDUCERS AND METHODS OF MANUFACTURING THE SAME

(71) Applicant: Samsung Electronics Co., Ltd., Suwon-si, Gyeonggi-do (KR)

(72) Inventors: Seogwoo Hong, Yongin-si (KR); Dongsik Shim, Hwaseong-si (KR); Seokwhan Chung, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 486 days.

(21) Appl. No.: 14/665,213

(22) Filed: Mar. 23, 2015

(65) Prior Publication Data

US 2016/0051226 A1 Feb. 25, 2016

(30) Foreign Application Priority Data

Aug. 25, 2014 (KR) ........................ 10-2014-0110954

(51) Int. Cl.
*A61B 8/00* (2006.01)
*H04R 31/00* (2006.01)
*B06B 1/02* (2006.01)

(52) U.S. Cl.
CPC ......... *H04R 31/006* (2013.01); *B06B 1/0292* (2013.01)

(58) Field of Classification Search
CPC .... H04R 31/006; B06B 1/0292; A61B 8/4494
See application file for complete search history.

(56) References Cited

U.S. PATENT DOCUMENTS

| | | | | |
|---|---|---|---|---|
| 8,540,640 | B2 | 9/2013 | Sano et al. | |
| 2011/0198970 | A1 | 8/2011 | Martin et al. | |
| 2016/0016197 | A1* | 1/2016 | Shim | B06B 1/0292 367/181 |
| 2016/0020709 | A1* | 1/2016 | Shim | B06B 1/0292 310/300 |
| 2016/0051226 | A1* | 2/2016 | Hong | H04R 31/006 600/459 |

FOREIGN PATENT DOCUMENTS

| | | | |
|---|---|---|---|
| JP | 2012227950 | A | 11/2012 |
| JP | 2014083281 | A | 5/2014 |
| KR | 10-2013-0021657 | A | 3/2013 |
| KR | 10-2013-0115656 | A | 10/2013 |

* cited by examiner

*Primary Examiner* — Daniel Pihulic
(74) *Attorney, Agent, or Firm* — Harness, Dickey & Pierce, P.L.C.

(57) ABSTRACT

An ultrasonic transducer module may comprise: an ultrasonic transducer comprising a substrate, a thin film separated from the substrate, a support portion for supporting the thin film, and a first electrode pad on the substrate; and/or a circuit board comprising a main body, an opening in the main body for accommodating the thin film, and a second electrode pad attached to the first electrode pad. An ultrasonic transducer may comprise: a substrate; a plurality of first electrode layers on the substrate, with spaces between the first electrode layers; an insulating layer between the substrate and the first electrode layers; a support portion on the first electrode layers; a thin film supported by the support portion, with cavities between each of the first electrode layers and the thin film; and/or a second electrode layer on the thin film.

20 Claims, 7 Drawing Sheets

ULTRASONIC TRANSDUCERS AND METHODS OF MANUFACTURING THE SAME

CROSS-REFERENCE TO RELATED APPLICATION(S)

This application claims priority from Korean Patent Application No. 10-2014-0110954, filed on Aug. 25, 2014, in the Korean Intellectual Property Office (KIPO), the entire contents of which are incorporated herein by reference.

BACKGROUND

1. Field

Some example embodiments may relate generally to ultrasonic transducer modules. Some example embodiments may relate generally to ultrasonic transducers. Some example embodiments may relate generally to methods of manufacturing the ultrasonic transducers.

2. Description of Related Art

Ultrasonic transducers such as micromachined ultrasonic transducers (MUTs) may convert electrical signals into ultrasound signals and vice versa. MUTs may be used in diagnostic medical imaging equipment to non-invasively obtain pictures or images of organs or tissues in a human body. MUTs may be classified into piezoelectric MUTs (pMUTs), capacitive MUTs (cMUTs), and magnetic MUTs (mMUTs) according to the conversion methods they use. Among the MUTs, the cMUTs may be mostly used.

A cMUT may transmit and receive ultrasound waves by using a displacement difference between hundreds or thousands of micromachined diaphragms. The cMUT may include a thin film on a silicon (Si) wafer used in a general semiconductor process, wherein a cavity is formed between the Si wafer and the thin film. The Si wafer, the thin film, and the cavity may form a capacitor. When an alternating current (AC) flows through the capacitor, the thin film may vibrate, and the vibration may generate ultrasonic waves. Accordingly, a patient's status may be safely and precisely observed based on the vibration of the cMUT's thin film.

SUMMARY

Some example embodiments may provide ultrasonic transducer modules having simplified assembling structures including an ultrasonic transducer mounted on a circuit board.

Some example embodiments may provide ultrasonic transducers having improved insulation characteristics between transducer elements.

Some example embodiments may provide methods of manufacturing the ultrasonic transducers.

In some example embodiments, an ultrasonic transducer module may comprise: an ultrasonic transducer comprising a substrate, a thin film separated from the substrate, a support portion for supporting the thin film, and a first electrode pad on the substrate; and/or a circuit board comprising a main body, an opening in the main body for accommodating the thin film, and a second electrode pad attached to the first electrode pad.

In some example embodiments, the first electrode pad may be attached to the second electrode pad by using a direct bonding method.

In some example embodiments, the first electrode pad may be attached to the second electrode pad by using flip chip bonding or surface mount technology.

In some example embodiments, the circuit board may further comprise a flexible connector extending from the main body.

In some example embodiments, the ultrasonic transducer may further comprise a plurality of first electrode layers between the substrate and the support portion at intervals from one another.

In some example embodiments, the ultrasonic transducer module may further comprise: an insulating layer coated on the first electrode layers.

In some example embodiments, the ultrasonic transducer module may further comprise: an adhesive layer between the substrate and the first electrode layers.

In some example embodiments, the adhesive layer may comprise metal or polymer.

In some example embodiments, the adhesive layer may comprise sound absorbing material.

In some example embodiments, the substrate may comprise a silicon substrate or a glass substrate.

In some example embodiments, the substrate may comprise porous material in a top portion facing the thin film.

In some example embodiments, an ultrasonic transducer may comprise: a substrate; a plurality of first electrode layers on the substrate, with spaces between the first electrode layers; an insulating layer between the substrate and the first electrode layers; a support portion on the first electrode layers; a thin film supported by the support portion, with cavities between each of the first electrode layers and the thin film; and/or a second electrode layer on the thin film.

In some example embodiments, the ultrasonic transducer may further comprise: an adhesive layer between the substrate and the first electrode layers.

In some example embodiments, the adhesive layer may comprise metal or polymer.

In some example embodiments, the adhesive layer may comprise sound absorbing material.

In some example embodiments, a method of manufacturing an ultrasonic transducer may comprise: forming a wafer comprising a first substrate, a first insulating layer, and a thin film; depositing a second insulating layer on the thin film; forming cavities in the second insulating layer by etching the second insulating layer; attaching a second substrate onto the second insulating layer; forming a plurality of first electrode layers that are electrically independent of one another by etching and penetrating the second substrate; depositing a third insulating layer on the first electrode layers; attaching a third substrate onto the third insulating layer; removing the first substrate and the first insulating layer; and/or forming a second electrode layer on the thin film.

In some example embodiments, the method may further comprise: forming an adhesive layer on the third insulating layer before the attaching of the third substrate.

In some example embodiments, the adhesive layer may comprise metal or polymer.

In some example embodiments, the adhesive layer may comprise sound absorbing material.

In some example embodiments, the third substrate may comprise porous material in a top portion facing the thin film.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
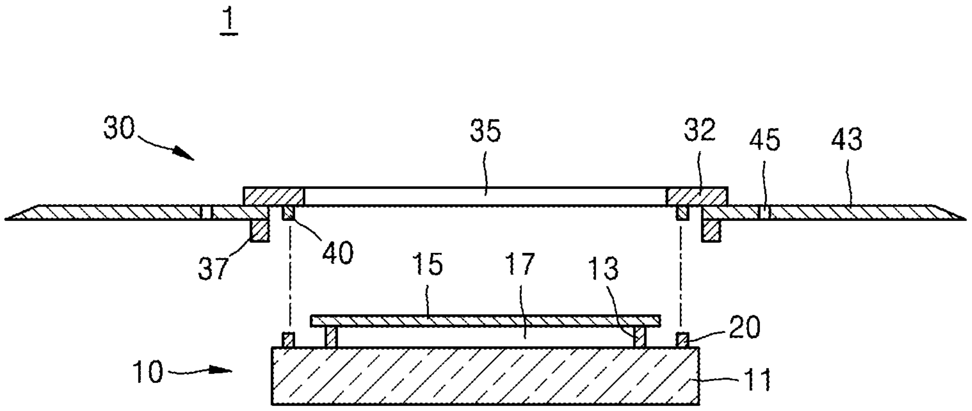
FIG. 1 is an exploded cross-sectional view of an ultrasonic transducer module according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIG. 1 is a cross-sectional view of an ultrasonic transducer module 1 according to some example embodiments.

Figure 2:
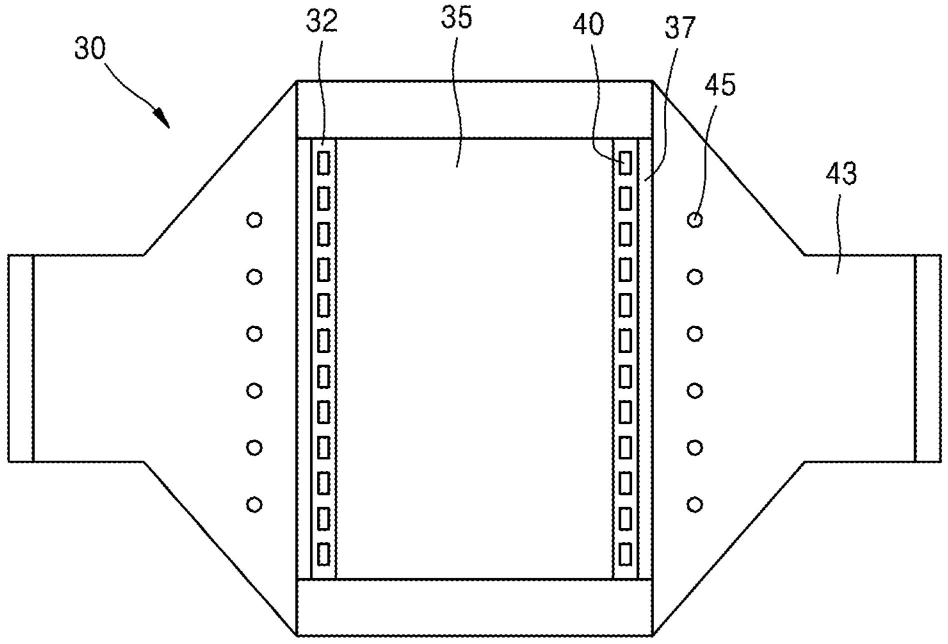
FIG. 2 is a bottom view of a circuit board for an ultrasonic transducer module according to some example embodiments.

Referring to FIG. 1, the ultrasonic transducer module 1 includes an ultrasonic transducer 10 and a circuit board 30 for supplying an electrical signal to the ultrasonic transducer 10. FIG. 2 is a bottom view of the circuit board 30.

The ultrasonic transducer 10 may further include a substrate 11, a thin film 15 spaced apart from the substrate 11, and a support portion 13 for supporting the thin film 15. A cavity 17 is formed between the substrate 11 and the thin film 15 in the ultrasonic transducer 10. When an electric current is applied to the substrate 11, the thin film 15 starts vibrating due to a change in a capacitance of the cavity 17 and, thus, ultrasound waves are generated.

FIG. 1 illustrates an example embodiment of the ultrasonic transducer 10. However, example embodiments are not limited thereto. As described above, the operating principle of the ultrasonic transducer 10 is that ultrasound waves are generated when the thin film 15 vibrates due to a change in capacitance, the thin film 15 oscillates in response to ultrasound waves from the outside, and such a change in vibrations of the thin film 15 is transformed into an electrical signal. The ultrasonic transducer 10 may have any structure as long as it operates according to the above operating principle.

The ultrasonic transducer 10 may also include a plurality of elements that are electrically independent of one another. For convenience of explanation, only one element is shown in the ultrasonic transducer 10 of FIG. 1. Each element may include at least one first electrode pad 20. An electrode structure will be described in greater detail below.

Referring to FIGS. 1 and 2, the circuit board 30 may include a main body 32 and a second electrode pad 40 disposed on one side of the main body 32. An opening 35 is formed in the main body 32. The circuit board 30 may be a printed circuit board (PCB). The opening 35 may be sufficiently large to receive the thin film 15. For example, when the ultrasonic transducer 10 is combined with the circuit board 30, the thin film 15 may be accommodated in the opening 35. Since the thin film 15 may be exposed through the opening 35, ultrasound waves may be generated or received by the thin film 15 without any interference due to the circuit board 30.

The second electrode pad 40 may be disposed at a position of the circuit board 30 corresponding to the first electrode pad 20. When the ultrasonic transducer 10 is combined with the circuit board 30, the first and second electrode pads 20 and 40 may be attached to each other using a direct bonding method. For example, the ultrasonic transducer 10 may be combined with the circuit board 30 by using a flip chip bonding or surface mount technology (SMT).

The main body 32 may further include a connector 43 that is engaged with an electrical driver (not shown). The connector 43 may be formed of a flexible material. For example, the connector 43 may include at least one hole 45 for receiving a fixing pin (not shown) for fixing the circuit board 30. The fixing pin may be preformed on a fixing jig so as to permit an accurate alignment between the first and second electrode pads 20 and 40 when the ultrasonic transducer is combined with the circuit board 30.

The connector 43 may be freely bent according to a position of a component to be connected thereto. The connector 43 may be fitted to the main body 32 by using various methods. For example, a fitting portion 37 may be disposed on a bottom edge of the main body 32, and one end of the connector 43 may be inserted between the main body 32 and the fitting portion 37. However, example embodiments are not limited thereto, and the connector 43 may be fitted to the main body 32 by using other various methods.

In some example embodiments, the ultrasonic transducer 10 may be attached to the circuit board 30 by using a direct bonding method without wire bonding. If wire bonding is used, a protective layer is required to cover a wire bonding structure. However, the protective layer may cover even the thin film 15 of the ultrasonic transducer 10, thereby reducing an effective region of the thin film 15 and increasing a thickness of the thin film 15. In some example embodiments, the ultrasonic transducer module 1 may be fabricated using direct bonding instead of wire bonding. Thus, an effective region of the thin film 15 may be maintained, and the ultrasonic transducer 10 may be simply attached to the circuit board 30.

Figure 3:
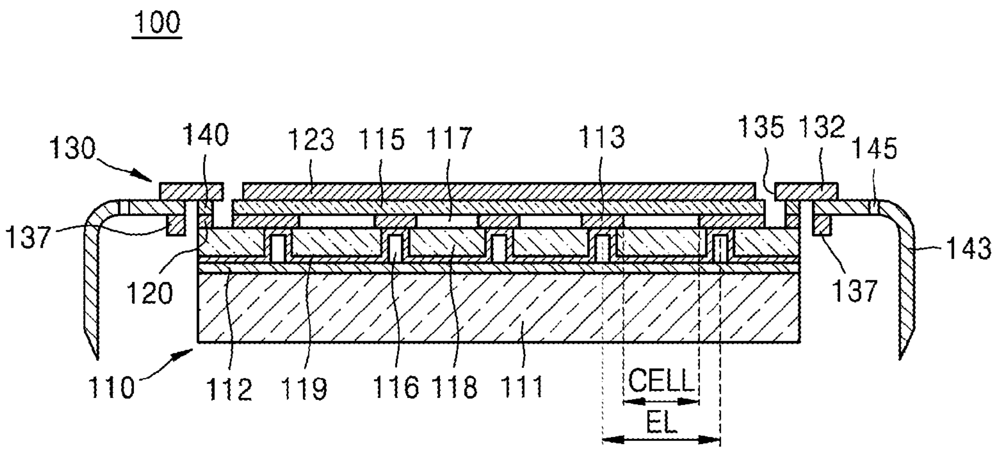
FIG. 3 illustrates an ultrasonic transducer module according to some example embodiments.

FIG. 3 illustrates an ultrasonic transducer module 100 according to some example embodiments.

Referring to FIG. 3, the ultrasonic transducer module 100 according to some example embodiments includes an ultrasonic transducer 110 and a circuit board 130.

The ultrasonic transducer 110 may include a substrate 111, a plurality of first electrode layers 118 formed on the substrate 111, a support portion 113 disposed on each of the first electrode layers 118, and a thin film 115 supported by the support portion 113.

For example, the substrate 111 may include a silicon substrate or a glass substrate. However, example embodiments are not limited thereto, and the substrate 111 may be any type of substrate suitable for a semiconductor process.

The first electrode layers 118 may be formed of an electrically conductive material. For example, the first electrode layers 118 may include a low-resistance silicon layer. The low-resistance silicon layer may have a low resistance due to its high doping concentration. For example, the low-resistance silicon layer may have resistivity of less than or equal to about 0.01 ohm-centimeter (Ω-cm). Adjacent ones of the first electrode layers 118 may be separated from one another for electrical isolation by a space 116 formed therebetween. Adjacent ones of the first electrode layers 118 may be electrically insulated from each other by the space 116. Regions where the first electrode layers 118 are electrically independent of one another are referred to as elements and will be described in more detail below with reference to FIG. 5.

The ultrasonic transducer 110 may further include a first insulating layer 119 formed between the substrate 111 and the first electrode layers 118. The first insulating layer 119 may be disposed between the substrate 111 and the first electrode layers 118 and along sidewalls of the first electrode layers 118. Thus, the first insulating layer 119 may improve insulation characteristics between the first electrode layers 118. The first insulating layer 119 may include oxide, such as silicon oxide, or nitride.

The thin film 115 is disposed above the first electrode layers 118 so that a cavity 117 is formed therebetween. The support portion 113 may include an insulating material. The thin film 115 may vibrate in response to a change in a capacitance of the cavity 117.

A second electrode layer 123 may be provided over the thin film 115 so as to cover the entire thin film 115. The second electrode layer 123 may include a conductive material such as silicon. For example, the first electrode layers 118 may operate as a signal electrode for applying a driving signal to each element, and the second electrode layer 123 may operate as a common ground electrode. When the ultrasonic transducer module 100 according to some example embodiments is used to examine a patient, the patient's safety is ensured even if a high voltage flows through the ultrasonic transducer module 100 because the second electrode layer 123, as the common ground electrode, faces the patient. The first electrode layers 118 may include at least one first electrode pad 120.

The circuit board 130 may include a main body 132, and a second electrode pad 140 disposed on one side of the main body 132. An opening 135 formed in the main body 132. The circuit board 130 may be a PCB. The opening 135 may be sufficiently large so that the thin film 115 may be exposed through the opening 135. For example, when the ultrasonic transducer 110 is combined with the circuit board 130, the thin film 115 may be accommodated in the opening 135. The first and second electrode pads 120 and 140 may be attached to each other using a direct bonding method. For example, the ultrasonic transducer 110 may be combined with the circuit board 130 by using flip chip bonding or SMT. The first and second electrode pads 120 and 140 may be formed of an electrically conductive material. For example, the first and second electrode pads 120 and 140 may be made of a metal, such as gold (Au), copper (Cu), tin (Sn), silver (Ag), aluminum (Al), platinum (Pt), titanium (Ti), nickel (Ni), chromium (Cr), or a combination thereof.

The main body 132 may further include a connector 143 that is engaged with an electrical driver (not shown). The connector 143 may be formed of a flexible material and include at least one hole 145. The connector 143 may be freely bent according to a position of a component to fit thereto. A fitting portion 137 may be disposed on a bottom edge of the main body 132, and one end of the connector 143 may be inserted between the main body 132 and the fitting portion 137. However, example embodiments are not limited thereto, and the connector 143 may be fitted to the main body 132 by using other various methods.

According to some example embodiments, since the thin film 115 is exposed via the opening 135 of the circuit board 130, and the first and second electrode pads 120 and 140 are attached to each other using a direct bonding method, it is easy to manufacture the ultrasonic transducer module 100. Furthermore, the ultrasonic transducer 110 may be combined with the circuit board 130 without any decrease in an effective region of the thin film 115.

In addition, as the first insulating layer 119 is formed around the spaces 116 between each of the first electrode layers 118, insulation characteristics between electrically independent elements is improved. Thus, electrical crosstalk between the elements may be reduced.

The ultrasonic transducer 110 may further include an adhesive layer 112 disposed between the substrate 111 and the plurality of first electrode layers 118. For example, the adhesive layer 112 may include a metal or polymer. Alternatively, the adhesive layer 112 may include a sound absorbing material. The sound absorbing material may be a porous material. The sound absorbing material may absorb ultrasound waves that are generated by vibration of the thin film 115 and propagate below the first electrode layers 118. Thus, it is possible to suppress ultrasound waves generated by vibration of the thin film 115 from being transmitted to an adjacent element through an area below the first electrode layers 118 and inducing crosstalk between the elements. Thus, it is also possible to reduce degradation in accuracy of ultrasound measurement.

Alternatively, crosstalk may be reduced by processing the substrate 111 to include a porous material. For example, an upper portion of the substrate 111 facing the thin film 115 may include a porous material.

In some example embodiments, the adhesive layer 112 may be disposed over the entire surface of the substrate 111 so as to reduce propagation of vibration of the thin film 115 to the substrate 111, thereby suppressing frequency distortions due to vibration of the substrate 111.

Figure 4:
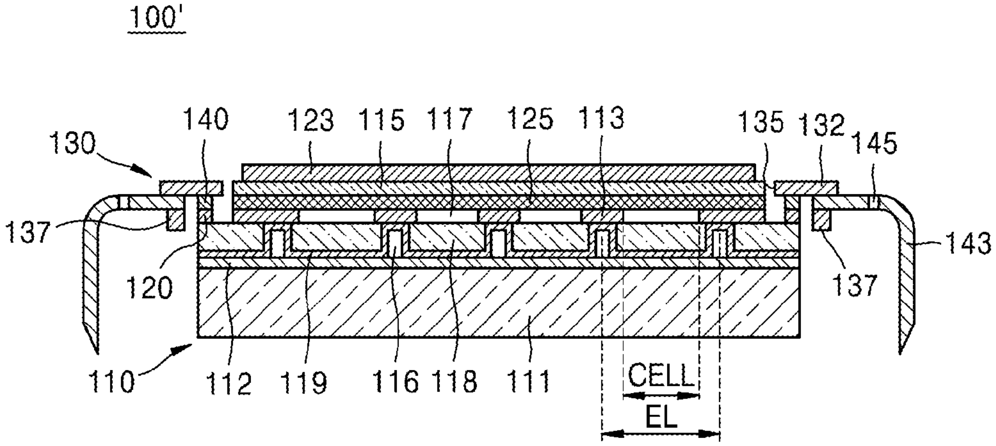
FIG. 4 illustrates an ultrasonic transducer module according to some example embodiments.

FIG. 4 illustrates an example embodiment that further includes a second insulating layer 125 in comparison to the ultrasonic transducer module 100 of FIG. 3. Since the other structure and operation of the ultrasonic transducer module 100' of FIG. 4 are the same as those of the ultrasonic transducer module 100 of FIG. 3, a detailed description thereof is omitted herein. The second insulating layer 125 may be disposed on a surface of the thin film 115 facing the cavity 117.

The second insulating layer 125 may prevent the thin film 115 from short-circuiting with the first electrode layers 118. Since the cavity 117 is small, the thin film 115 may contact the first electrode layers 118 during vibration thereof. In some example embodiments, the second insulating layer 125 may prevent the thin film 115 and the first electrode layers 118 from electrically short-circuiting with each other.

Figure 5:
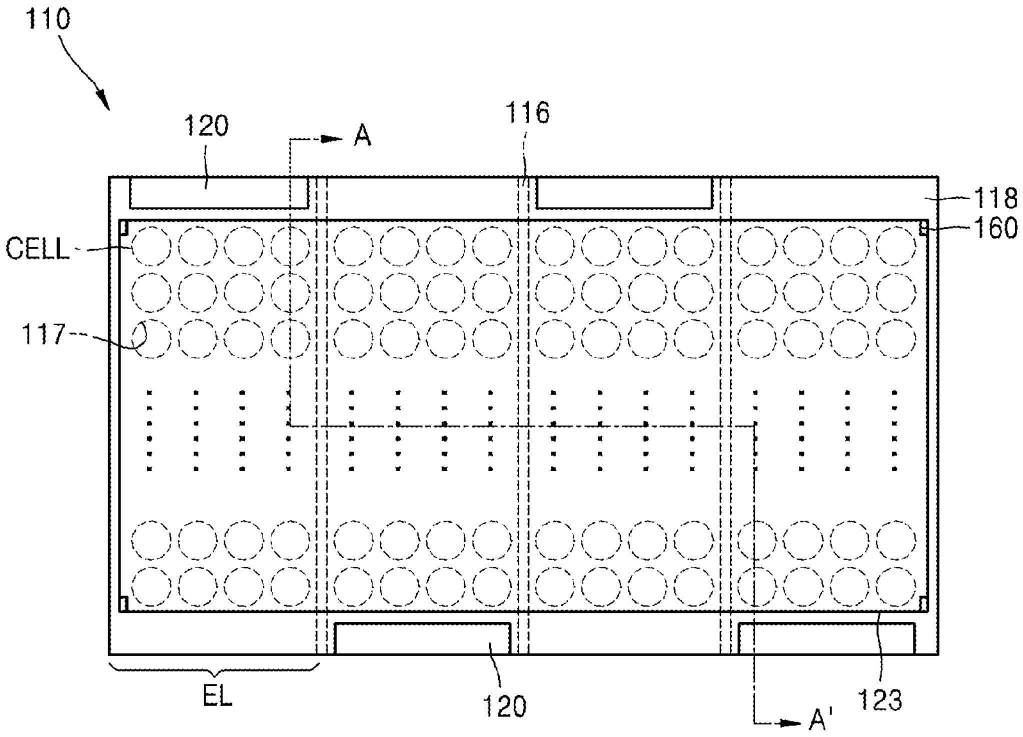
FIG. 5 is a schematic plan view of an ultrasonic transducer according to some example embodiments.

FIG. 5 is a schematic plan view of an ultrasonic transducer 110 according to some example embodiments. The ultrasonic transducer 110 may include a plurality of elements EL that operate electrically independently from one another. The plurality of elements EL may be arranged in one-dimensional (1D) array. Each of the plurality of elements EL may include at least one cell CELL. A cell CELL may be the smallest ultrasonic vibration unit defined by a cavity 117. Although FIG. 5 shows that a cell CELL has a circular cross-section, example embodiments are not limited thereto, and the cell CELL may have other various cross-sectional shapes such as quadrangular and other polygonal shapes.

FIG. 5 is a schematic diagram illustrating a relationship between an element EL, a cell CELL, and an electrode structure. The ultrasonic transducer module 100' according to some example embodiments is not completely the same as the ultrasonic transducer module 100 of FIG. 3. FIG. 4 is a cross-sectional view of the ultrasonic transducer 110 taken along line A-A' of FIG. 5. For convenience, FIG. 5 illustrates only one cell CELL for each element EL, and an example embodiment where a plurality of elements EL are separated from each other by a space 116 and each element EL includes one first electrode pad 120. A position of the first electrode pad 120 may be changed alternately for every element EL. However, example embodiments are not limited to this structure, and an electrode structure or the number of the electrodes may be different. Furthermore, the second electrode layer 123 may include at least one third electrode pad 160 (e.g., at each corner thereof).

An operation of the ultrasonic transducer module 100/100' according to some example embodiments will now be described in detail with reference to FIGS. 3 and 4.

When a direct current (DC) voltage is applied to the first and second electrode layers 118 and 123 via the first through third electrode pads 120, 140, and 160, the thin film 115 may be located at a height where an electrostatic force between the first and second electrode layers 118 and 123 and a gravitational force acting on the thin film 115 are in equilibrium. Furthermore, when an alternating current (AC) voltage is applied to the first and second electrode layers 118 and 123, the thin film 115 may vibrate due to a variation in an electrostatic force between the first and second electrode layers 118 and 123. Due to the vibration, an ultrasound signal may be transmitted from the thin film 115. Next, a reception operation of the ultrasonic transducer module 100/100' will be described. When a second DC voltage is applied to the first and second electrode layers 118 and 123 via the first through third electrode pads 120, 140, and 160 for initialization of the ultrasonic transducer module 100/100', the thin film 115 may be located at a height where an electrostatic force between the first and second electrode layers 118 and 123 and a gravitational force acting on the thin film 115 are in equilibrium. In this state, when an external physical signal (e.g., an acoustic signal), is input to the thin film 115, the thin film 115 vibrates and, thus, the electrostatic force between the first and second electrode layers 118 and 123 may change. The ultrasonic transducer module 100/100' may detect the external acoustic signal by sensing the changed electrostatic force.

A method of manufacturing an ultrasonic transducer according to an some example embodiment will now be described in detail with reference to FIGS. 6 through 15.

Figure 6:
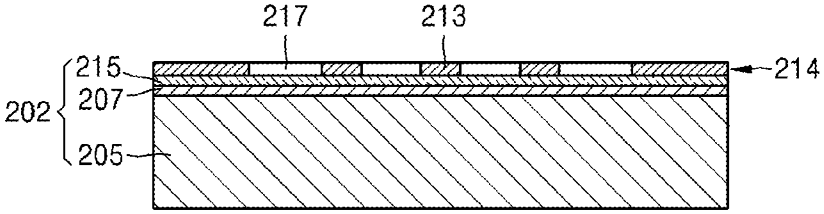
FIGS. 6 through 15 illustrate a method of manufacturing an ultrasonic transducer according to some example embodiments.

Referring to FIG. 6, a first insulating layer 207 is deposited on a first substrate 205 and a thin film 215 is deposited on the first insulating layer 207. The first substrate 205 and the thin film 215 may include silicon. In some example embodiments, a wafer including the first substrate 205, the first insulating layer 207, and the thin film 215 may be prepared. For example, the first substrate 205, the first insulating layer 207, and the thin film 215 may be formed as a first Silicon-On-Insulator (SOI) wafer 202.

Figure 7:
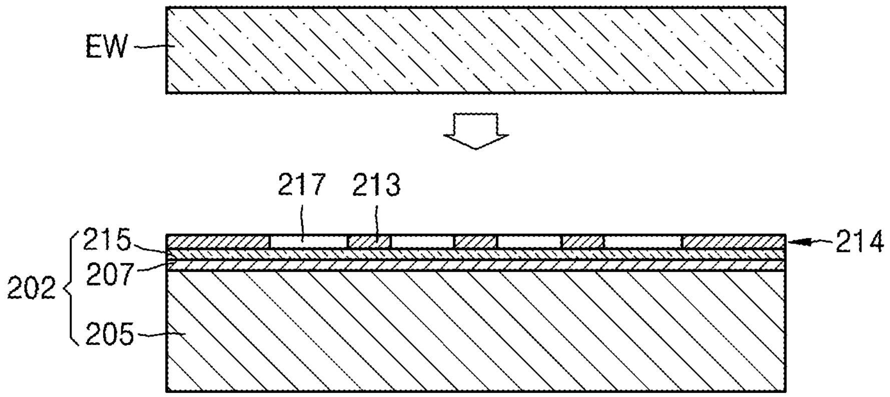

A second insulating layer 214 may be deposited on the thin film 215. The second insulating layer 214 may be formed of oxide or nitride and etched to form cavities 217 for exposing the thin film 215. In some example embodiments, a portion of the second insulating layer 214 remaining after the etching may be a support portion 213 for supporting the thin film 215. Referring to FIG. 7, a second substrate EW may be prepared. The second substrate EW may include an electrically conductive material. For example, the second substrate EW may be a low-resistance silicon substrate. A low-resistance silicon may have a resistivity of less than or equal to about 0.01 Ω-cm. However, example embodiments are not limited thereto, and the second substrate EW may be formed of other various conductive materials. The second insulating layer 214 may be attached to the second substrate EW by using a silicon direct bonding method. However, example embodiments are not limited thereto, and other various bonding techniques may be used.

Figure 8:
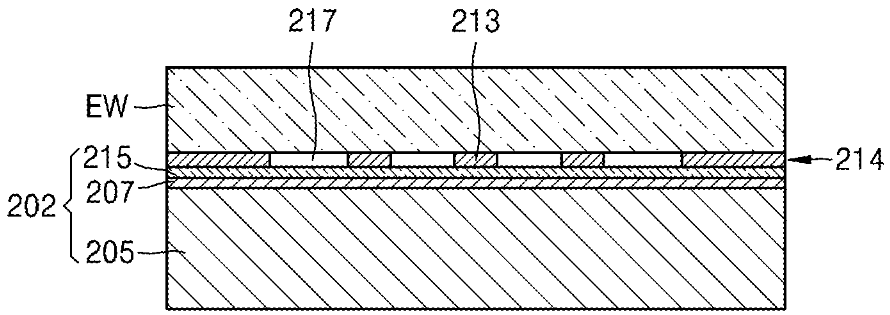
Figure 9:
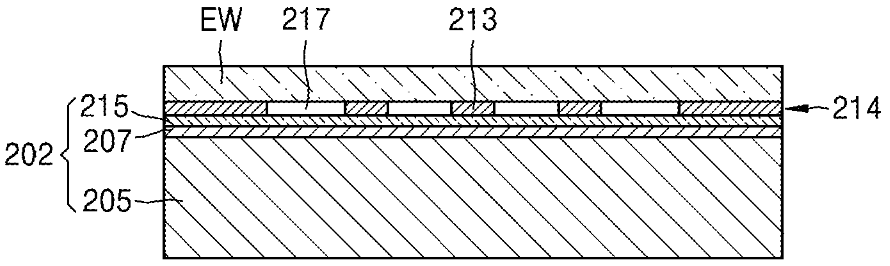
Figure 10:
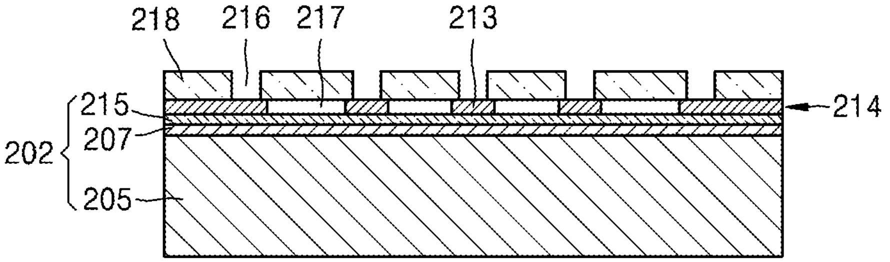

Referring to FIG. 8, the second substrate EW may be attached onto the etched second insulating layer 214. Referring to FIG. 9, the second substrate EW may be polished to have a reduced thickness. However, if the second substrate EW is etched to form through-holes, the polishing of the second substrate EW may be omitted. Referring to FIG. 10, the second substrate EW is etched and penetrated to form spaces 216 and a plurality of first electrode layers 218 that are electrically independent of one another due to the spaces 216. Elements (EL in FIG. 5) that are electrically insulated regions may be separated from one another by the spaces 216.

Figure 11:
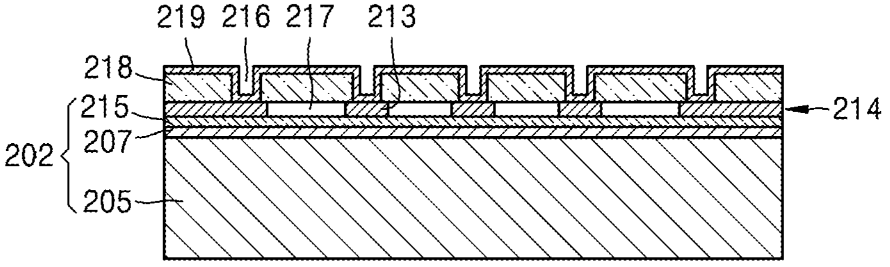
Figure 12:
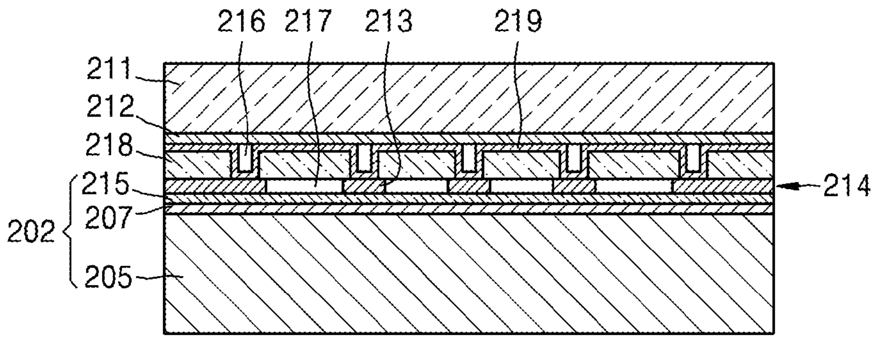

Referring to FIG. 11, a third insulating layer 219 may be deposited on the first electrode layers 218 to improve insulation characteristics between the elements and also reduce crosstalk therebetween. Referring to FIG. 12, a third substrate 211 may be attached onto the third insulating layer 219. For example, the third substrate 211 may include a silicon substrate or a glass substrate. An adhesive layer 212 may be used to bond the third substrate 211 to the third insulating layer 219. The adhesive layer 212 may include a metal or polymer. Alternatively, the adhesive layer 212 may include a sound absorbing material. The sound absorbing material may include a porous material.

The third substrate 211 may also include a porous material in a portion that is in contact with the adhesive layer 212.

Figure 13:
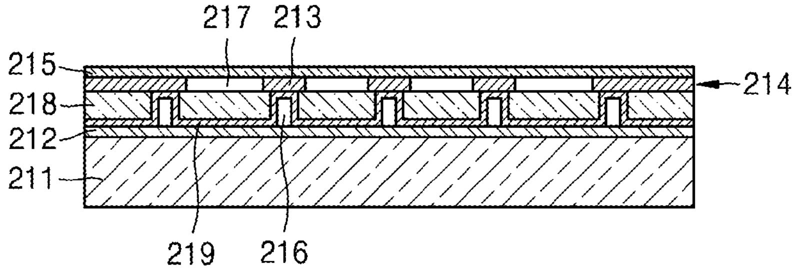
Figure 14:
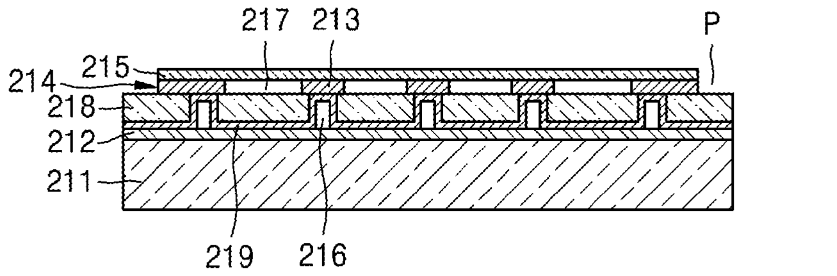
Figure 15:
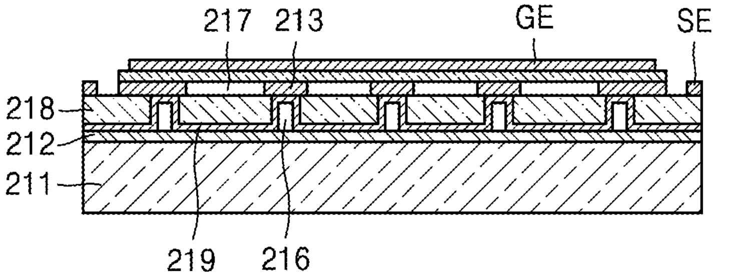

Referring to FIG. 13, the structure of FIG. 12 may be turned over to remove the first substrate 205 and the first insulating layer 207. Thus, the thin film 215 may be located at the top of the resultant structure. Referring to FIG. 14, the thin film 215 and the second insulating layer 214 are etched to create a pattern P for forming an electrode pad. A conductive material layer may be deposited on the resultant structure of FIG. 14 to form a first electrode pad SE and a second electrode layer GE as shown in FIG. 15. The first electrode pad SE may apply a signal voltage to the first electrode layers 218. The second electrode layer GE may serve as a common ground electrode.

The pattern P may have various shapes. For example, the pattern P may have an open top and an open one side, or may be formed as a groove with an open top. The circuit board 30 shown in FIG. 1 may be combined with the ultrasonic transducer manufactured using the method according to some example embodiments.

Figure 16:
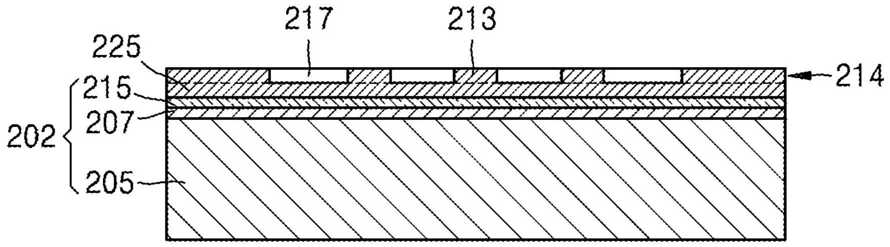
FIGS. 16 and 17 illustrate a method of manufacturing an ultrasonic transducer according to some example embodiments.
Figure 17:
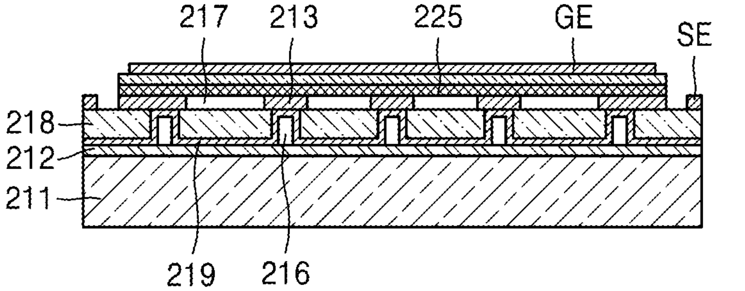

According to some example embodiments, referring to FIG. 16, a fourth insulating layer 225 may be further deposited on the thin film 215, and the second insulating layer 214 may be deposited on the fourth insulating layer 225. After depositing the second insulating layer 214 on the fourth insulating layer 225, subsequent processes may be performed as described above with reference to FIGS. 6 through 15. Referring to FIG. 17, the fourth insulating layer 225 may be formed on a surface of the thin film 215 that faces the cavities 217.

The fourth insulating layer 225 may prevent the thin film 215 from short-circuiting with the first electrode layers 218. In detail, since the cavity 217 is small, the thin film 215 may vibrate and contact the first electrode layers 218. In some example embodiments, the fourth insulating layer 225 may prevent the thin film 215 and the first electrode layers 218 from electrically short-circuiting with each other.

According to the methods of manufacturing an ultrasonic transducer according to some example embodiments, an insulating layer may be formed on a first electrode layer, thereby improving insulation characteristics between elements. Furthermore, an ultrasonic transducer is configured so that an electrode layer acting as a common ground electrode may face a human body, thereby improving safe use of the ultrasonic transducer.

Some example embodiments of ultrasonic transducer modules, ultrasonic transducers, and methods of manufacturing the ultrasonic transducers according to some example embodiments have been described with reference to the appended figures.

It should be understood that the example embodiments described herein should be considered in a descriptive sense only and not for purposes of limitation. Descriptions of features or aspects within each embodiment should typically be considered as available for other similar features or aspects in other embodiments.

While some example embodiments of the present inventive concept have been described with reference to the figures, it will be understood by those of ordinary skill in the art that various changes in form and details may be made herein without departing from the spirit and scope of the present inventive concept as defined by the following claims.

What is claimed is:

1. An ultrasonic transducer module, comprising:

an ultrasonic transducer comprising a substrate, a thin film separated from the substrate, a support portion for supporting the thin film, and a first electrode pad on the substrate; and a circuit board comprising a main body, an opening in the main body for accommodating the thin film, and a second electrode pad attached to the first electrode pad.

2. The ultrasonic transducer module of claim 1, wherein the first electrode pad is attached to the second electrode pad by using a direct bonding method.

3. The ultrasonic transducer module of claim 1, wherein the first electrode pad is attached to the second electrode pad by using flip chip bonding or surface mount technology.

4. The ultrasonic transducer module of claim 1, wherein the circuit board further comprises a flexible connector extending from the main body.

5. The ultrasonic transducer module of claim 1, wherein the ultrasonic transducer further comprises a plurality of first electrode layers between the substrate and the support portion at intervals from one another.

6. The ultrasonic transducer module of claim 5, further comprising:

an insulating layer coated on the first electrode layers.

7. The ultrasonic transducer module of claim 5, further comprising:

an adhesive layer between the substrate and the first electrode layers.

8. The ultrasonic transducer module of claim 7, wherein the adhesive layer comprises metal or polymer.

9. The ultrasonic transducer module of claim 7, wherein the adhesive layer comprises sound absorbing material.

10. The ultrasonic transducer module of claim 1, wherein the substrate comprises a silicon substrate or a glass substrate.

11. The ultrasonic transducer module of claim 1, wherein the substrate comprises porous material in a top portion facing the thin film.

12. An ultrasonic transducer, comprising:

a substrate;

a plurality of first electrode layers on the substrate, with spaces between the first electrode layers;

an insulating layer between the substrate and the first electrode layers;

a support portion on the first electrode layers;

a thin film supported by the support portion, with cavities between each of the first electrode layers and the thin film; and a second electrode layer on the thin film.

13. The ultrasonic transducer of claim 12, further comprising:

an adhesive layer between the substrate and the first electrode layers.

14. The ultrasonic transducer of claim 13, wherein the adhesive layer comprises metal or polymer.

15. The ultrasonic transducer of claim 13, wherein the adhesive layer comprises sound absorbing material.

16. A method of manufacturing an ultrasonic transducer, the method comprising:

forming a wafer comprising a first substrate, a first insulating layer, and a thin film;

depositing a second insulating layer on the thin film;

forming cavities in the second insulating layer by etching the second insulating layer;

attaching a second substrate onto the second insulating layer;

forming a plurality of first electrode layers that are electrically independent of one another by etching and penetrating the second substrate;

depositing a third insulating layer on the first electrode layers;

attaching a third substrate onto the third insulating layer;

removing the first substrate and the first insulating layer; and forming a second electrode layer on the thin film.

17. The method of claim 16, further comprising:

forming an adhesive layer on the third insulating layer before the attaching of the third substrate.

18. The method of claim 17, wherein the adhesive layer comprises metal or polymer.

19. The method of claim 17, wherein the adhesive layer comprises sound absorbing material.

20. The method of claim 16, wherein the third substrate comprises porous material in a top portion facing the thin film.

* * * * *